United States Patent [19]

Moller et al.

[11] 4,143,159

[45] Mar. 6, 1979

[54] SKIN-CARE AGENTS CONTAINING HYDROXYALKYL CARBOXAMIDES AND PROCESS

[75] Inventors: Hinrich Möller, Düsseldorf-Benrath; Rainer Osberghaus, Düsseldorf-urdenbach, both of Fed. Rep. of Germany

[73] Assignee: Henkel Kommanditgesellschaft auf Aktien, Düsseldorf-Holthausen, Fed. Rep. of Germany

[21] Appl. No.: 814,049

[22] Filed: Jul. 8, 1977

[30] Foreign Application Priority Data

Jul. 12, 1976 [DE] Fed. Rep. of Germany ....... 2631284

[51] Int. Cl.$^2$ ............................................... A61K 7/48
[52] U.S. Cl. ..................................... 424/358; 424/320
[58] Field of Search ........................................ 424/358

[56] References Cited

U.S. PATENT DOCUMENTS

| 3,970,584 | 7/1976 | Hart et al. | 252/305 |
| 4,064,268 | 12/1977 | Adolphi et al. | 424/308 |

OTHER PUBLICATIONS

King; Chem. Evaluated as insecticides and repellents at Orlando, Fla. May 1954, pp. 1, 13–16, 92, 93, 94, 182, 205, 206, 284 and 285.

*Primary Examiner*—Allen J. Robinson
*Attorney, Agent, or Firm*—Hammond & Littell

[57] ABSTRACT

Skin-care, skin-protection, and skin-cleaning agent compositions containing at least one hydroxyalkyl carboxamide as a skin-moisturizing agent, as well as a process for protecting the skin utilizing this composition.

24 Claims, No Drawings

SKIN-CARE AGENTS CONTAINING HYDROXYALKYL CARBOXAMIDES AND PROCESS

THE PRIOR ART

It is generally known that the protective measures for healthy skin include, among other things, that the skin surface maintains a certain hygroscopicity. When the substances, on which this hygroscopicity and its continuous restoration are based, are removed from the skin by environmental influences, such as repeated washing with substances having highly wetting and extracting effects, chemical influences and the strong effects of weathering, the epidermis is subjected to changes which can greatly reduce the protective action of the skin against injurious environmental influences.

Therefore, the task arose of providing cosmetic agents, particularly agents for the care, protection and cleaning of the skin, by means of which the ability of the skin to function is fully maintained or enhanced despite the injurious environmental influences, and by means of which the restoration of the epidermis is effectively assisted when damage to the skin has occurred.

The products hitherto used as agents for keeping the skin moist were, without exception, ionic compounds such as acids and, primarily salts, which, although they produced reliable results as skin moisture regulators in many cases, frequently caused difficulties when incorporated in the cosmetic preparations, especially if the bases were sensitive emulsions. In such cases, it was frequently not possible to incorporate fully adequate quantities of skin moisture regulators. Furthermore, in addition to the general task of developing satisfactory agents for keeping the skin moist, a particular interest was attached to developing products which do not cause any difficulties even when they are incorporated in more sensitive cosmetic emulsions.

OBJECTS OF THE INVENTION

It is an object of the present invention to provide a skin-care, skin-protection, and skin-cleaning agent composition containing at least one hydroxyalkane carboxylic acid amide as a skin moisturizing agent.

It is another object of the present invention to provide a skin-care and skin-protection agent composition, by means of which the functional capacity of the skin may be maintained or increased in spite of harmful environmental influences, and which effectively supports the restoration of the horny layer, should any damage have been incurred.

These and further objects of the invention will become apparent as the description thereof proceeds.

DESCRIPTION OF THE INVENTION

The present invention relates to skin-care, skin-protection and skin-cleaning agent compositions containing at least one hydroxyalkane carboxylic acid amide as a skin moisturizing agent.

Accordingly, the present invention involves cosmetic agents, particularly agents for the care, protection and cleaning of the skin, comprising conventional constituents, such as surfactants, emulsifiers, fatty substances, vegetable extracts, solvents, perfumes, thickening agents, and preservatives, and from 1 to 20 percent by weight, preferably 3 to 10 percent by weight, relative to the total weight of the cosmetic agent, of at least one hydroxyalkane carboxylic acid amide of the formula

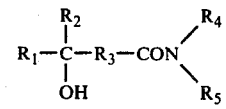

wherein $R_1$ and $R_2$ are independently of each other a member selected from the group consisting of hydrogen and an alkyl radical having 1 to 4 carbon atoms, $R_3$ is a member selected from the group consisting of the direct bond, a straight-chain alkylene radical having 1 to 3 carbon atoms and a straight-chain alkylene radical having 1 to 3 carbon atoms substituted by one or more alkyl and/or hydroxyalkyl groups and $R_4$ and $R_5$ independently of one another are a member selected from the group consisting of hydrogen, an alkyl radical having 1 to 4 carbon atoms and an hydroxyalkyl radical having 2 to 6 carbon atoms and 1 to 5 hydroxyl groups.

$R_1$ and $R_2$ can each very suitably be hydrogen or methyl. The straight-chain alkylene radical $R_3$ can, for example, be substituted by 1 to 4 groups selected from alkyl of 1 to 4, preferably 1, carbon atoms, hydroxyalkyl of 1 to 4, preferably 1, carbon atoms or any combination of said alkyl and hydroxyalkyl groups.

More particularly, the present invention provides a cosmetic agent composition for the care and protection of the skin of warm-blooded animals consisting essentially of from 1% to 20% by weight based upon the total weight of at least one hydroxyalkane carboxylic acid amide of the formula

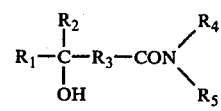

wherein $R_1$ and $R_2$ are independently of each other a member selected from the group consisting of hydrogen and an alkyl radical having 1 to 4 carbon atoms, $R_3$ is a member selected from the group consisting of the direct bond, a straight-chain alkylene radical having 1 to 3 carbon atoms and a straight-chain alkylene radical having 1 to 3 carbon atoms substituted by one or more alkyl and/or hydroxyalkyl groups and $R_4$ and $R_5$ independently of one another are a member selected from the group consisting of hydrogen, an alkyl radical having 1 to 4 carbon atoms and an hydroxyalkyl radical having 2 to 6 carbon atoms and 1 to 5 hydroxyl groups; and the remainder conventional cosmetic excipients.

In addition the present invention provides a process for the care and protection of the skin of warm-blooded animals comprising topically applying to the skin a safe but effective amount of the agent composition mentioned above.

The hydroxyalkyl carboxamides which are used in the agent compositions of the invention are extremely suitable for maintaining or restoring the water retention of the skin and thus for keeping the skin soft, flexible and fully capable of performing its function.

The compounds of the invention can be produced by generally known methods. Thus, for example, they can be obtained by aminolysis of the alkyl esters or lactones of the corresponding hydroxyalkanoic acids in a solvent-free method or in solvents such as alkanols, dioxane or tetrahydrofuran. Furthermore, the hydroxyalkyl carboxamides can be obtained from the hydroxyalkanoic acids and the corresponding amines by heating these reactants to higher temperatures, with or without solvents. Solvents for the azeotropic separation of water, may be, for example, toluene, xylene, chlorobenzene or ligroin.

Examples of hydroxyalkyl carboxamides to be used in accordance with the invention are glycolic acid amide, lactic acid amide, α-hydroxybutyric acid amide, β-hydroxybutyric acid amide, γ-hydroxybutyric acid amide, α-hydroxyisobutyric acid amide, β-hydroxyisobutyric acid amide, α-hydroxyvaleric acid amide, γ-hydroxyvaleric acid amide, and α,α-bis-hydroxymethylpropionic acid amide.

Further examples are the following N-substituted and N,N-disubstituted derivatives of glycolic acid amide: the N-methyl-, N-ethyl-, N-propyl-, N,N-dimethyl-, N,N-diethyl-, N-butyl-, N-(2-hydroxyethyl)-, N-(2-hydroxypropyl)-, N-(3-hydroxy-propyl)-, N-(2-hydroxybutyl)-, N-(1-hydroxy-2-methyl-2-propyl)-, N-(2,3-dihydroxypropyl)-, N-(1,3-dihydroxy-2-propyl)-, N-(1,3-dihydroxy-2-methyl-2-propyl)-, N-(1,3-dihydroxy-2-ethyl-2-propyl)-, N-(trishydroxymethyl-methyl)-, N-(2-hydroxyethyl)-N-methyl-, N-(2-hydroxypropyl)-N-methyl-, N-(2,3-dihydroxypropyl)-N-ethyl-, N-(2,3,4,5,6-pentahydroxy-hexyl)-, N-(1,3,4,5,6-pentahydroxy-2-hexyl)-, N,N-bis-(2-hydroxyethyl)-, N,N-bis-(2-hydroxypropyl)-, and N-(2-hydroxyethyl)-N-(2-hydroxypropyl)-derivatives. Other useful carboxamides of the invention are the above analogous N- substituted and N,N-disubstituted derivatives of each of the following hydroxyalkyl carboxamides: lactic acid amide, α-hydroxybutyramide, β-hydroxybutyramide, γ-hydroxybutyramide, α-hydroxyisobutyramide, β-hydroxyisobutyramide, α-hydroxyvaleramide, α-hydroxy-valeramide, and α-α-bis-hydroxymethyl-propionamide, i.e., N-methyl-lactic acid amide, N-ethyl-lactic acid amide, N-propyl-lactic acid amide, etc.

Very advantageous results have been obtained with those hydroxyalkyl carboxylic acid amides of the invention wherein $R_4$ is hydroxyalkyl and $R_5$ is hydrogen or both $R_4$ and $R_5$ are hydroxyalkyl. It has also been found that good results can be obtained by having one or more hydroxyalkyl groups on the $R_3$ alkylene radical. The hydroxymethyl group is an example of such an especially suitable hydroxyalkyl substituent.

The hydroxyalkyl carboxamides of the invention are colorless to bright yellow colored, crystalline or highly viscous, fully stable products, which have very satisfactory physiological compatibility and, acting as neutral, non-ionic compounds, are distinguished by the fact that they can be incorporated in cosmetic emulsion bases in a particularly satisfactory manner.

It was found that the functional capacity of the skin may be maintained or restored even to a higher degree than before if it is treated with agents for the care and protection of the skin, which besides the customary constituents include from 1% to 20% by weight, preferably 3% to 10% by weight, based on the total composition of the hydroxyalkane carboxylic acid amides in accordance with the invention.

Among the compositions for the care and protection of the skin having special skin-caring properties due to the addition of the hydroxyalkane carboxylic acid amides used in accordance with the invention are emulsions of the oil-in-water type or water-in-oil type.

Examples of agents for the care, protection and cleaning of the skin, to which special skin-care properties are imparted by the addition of the hydroxyalkane carboxylic acid amides of the invention are the conventional day creams, baby creams, night and nutrient creams, cleansing creams, skin protection creams, glycerol creams, creams having special additives of animal and vegetable origin, creams and emulsions for protection against the sun and sun tanning creams, soaps, bath oils, foam baths, shower baths, face lotions, and after-shave lotions. They can be incorporated in the agents for the care, protection and cleansing of the skin in a known manner simply by stirring-in or dissolving. In addition to the amides of hydroxyalkane carboxylic acids used in accordance with the invention, the cosmetic preparations can also contain conventional quantities of the constituents usually contained therein, such as emulsifiers, fatty substances, vegetable extracts, thickeners, preservatives, surfactants, perfumes and solvents. Water and lower alcohols, such as methanol, ethanol and isopropanol, serve as very useful constitutents of the cosmetic preparations of the invention. Lower alcohols of 1-3 carbon atoms are very suitable. The pH value of the agents for the care and protection of the skin may be in the range of acid to neutral (approximately pH 5–7.0) and, advantageously, is adjusted to a weakly acid value of approximately pH 6. The skin cleansing agents based on soap should be adjusted so as to have as weak an alkaline pH value as possible.

The following examples are intended to illustrate the subject of the invention without, however, limiting it to these examples.

EXAMPLES

The production of some of the amides of hydroxyalkane carboxylic acids of the invention is described below.

EXAMPLE 1

Product A2: N-propyl-lactic acid amide [J.Org.Chem. 15,317(1950)]

A mixture of 35.4 gm (0.3 mole) of ethyl lactate and 19.4 gm (0.33 mole) of propylamine were stirred together at 60° C. for 16 hours and subsequently distilled under reduced pressure. 30 gm (76% of theory) of N-propyl-lactic acid amide of boiling point 152° C./9 torr and of refractive index ($n_D^{20}$) 1.4563 were obtained.

Product A3: N-(2-hydroxyethyl)-lactic acid amide

A mixture of 70.8 gm (0.6 mole) of ethyl lactate and 36.6 gm (0.6 mole) of ethanolamine were stirred together at 60° C. for 16 hours, and the ethanol formed was subsequently distilled off under reduced pressure. 71 gm (89% of theory) of light yellow, viscous N-(2-hydroxyethyl)-lactic acid amide of refractive index ($n_D^{20}$) 1.4850 were obtained.

Product B1: N-(2-hydroxyethyl)-γ-hydroxybutyramide

A solution of 24.4 gm (0.4 mole) of ethanolamine in 30 ml of methanol were slowly added dropwise with stirring to a solution of 34.4 gm (0.4 mole) of γ - butyrolactone in 50 ml of methanol. The temperature rose to 50° C. The mixture was subsequently heated for 3 hours at boiling and the methanol was distilled off under reduced pressure. A quantitative yield of N-(2-hydroxyethyl)-γ-hydroxybutyramide was obtained in the form of a colorless viscous liquid. The compound became crystalline after standing for a long period of time and melts at 54° to 56° C.

The following amides of hydroxyalkane carboxylic acids were produced in accordance with the methods described in the above Examples. Reaction parameters, properties and some literature references are presented in TABLE 1 below for the amides. Products A2, A3 and B1 are also included in the table.

TABLE 1

| Product | Reaction Conditions Temp. °C | Time Hours | Solvent | Properties m.p. or b.p. (°C/torr); $n_D^{20}$ | Recrystallized from | Remarks, Literature References |
|---|---|---|---|---|---|---|
| A1: Lactic acid amide | — | — | — | 70 | Ethylacetate | Beilst. 3 II 208 |
| A2: N-propyl lactic acid amide | 60 | 16 | — | 152/9 1.4563 | — | J.O.C. 15, 317 (1950) |
| A3: N-(2-hydroxyethyl) lactic acid amide | 60 | 16 | — | 1.4850 | — | Light yellow, viscous oil |
| A4: N-(2-hydroxypropyl) lactic acid amide | 60 | 16 | — | 1.4773 | — | Light yellow, viscous oil |
| A5: N-(2-hydroxy-isobutyl) lactic acid amide | 80 | 8 | — | 1.4741 | — | Light yellow, viscous oil Product extracted with not ether |
| A6: N-(1,3-dihydroxy-2-methyl-2-propyl) lactic acid amide | 80 | 8 | — | 79–80 | 2-propanol/ petroleum ether | |
| A7: N-(tris-hydroxy-methyl-methyl) lactic acid amide | 80 | 6 | — | 1.5057 | — | Light yellow, viscous oil |
| A8: N,N-bis-(2-hydroxyethyl) lactic acid amide | 60 | 16 | — | 1.4818 | — | Colorless resin |
| A9: N,N-bis-(2-hydroxypropyl)lactic acid amide | 60 | 16 | — | 1.5011 | — | |
| B1: N-(2-hydroxyethyl-γ-hydroxy-butyra-amide | 65 | 3 | Methanol | 54–56 | — | Precipitated as a colorless resin |
| B2: N-(2-hydroxypropyl)-γ-hydroxy-butyramide | 65 | 3 | Methanol | 1.4889 | — | Colorless resin |
| B3: N-(2-hydroxy-isobutyl)-γ-hydroxy-butyramide | 78 +120 | 6 4 | Ethanol | 1.4870 | — | Colorless resin |
| B4: N-(1,3-dihydroxy-2-methyl-2-propyl)-γ-hydroxy-butyramide | 78 +120 | 6 4 | Ethanol | 1.4981 | — | Light yellow, viscous oil |
| B5: N-(tris-hydroxy-methyl-methyl-γ-hydroxy-butyr-amide | 78 | 8 | Ethanol | 88–90 | — | Colorless resin |
| B6: N,N-bis-(2-hydroxy-ethyl-γ-hydroxy-butyramide | 78 +120 | 6 5 | Ethanol | 1.5049 | — | Light yellow, viscous oil |
| B7: N,N-bis-(2-hydroxy-propyl)-γ-hydroxy-butyramide | 78 +120 | 6 6 | Ethanol | 1.4891 | — | Light yellow, viscous oil |
| C1: N-(2-hydroxyethyl)-α-hydroxy-iso-butyramide | 60 +70 | 16 9 | — | 138–140/0.01 1.4778 | — | Colorless, viscous oil |
| C2: N-(2-hydroxypropyl)- | 66 | 16 | | 136/0.01 | | |

TABLE 1-continued

| Product | Reaction Conditions | | | Properties m.p. or b.p. ($°C$/torr); $n_D^{20}$ | Recrystal- lized from | Remarks, Litera- ture References |
|---|---|---|---|---|---|---|
| | Temp. °C | Time Hours | Solvent | | | |
| α-hydroxy isobutyramide | +70 | 9 | | 64–65 | — | Colorless |
| C3: N-(2-hy- droxy-iso- butyl)-α- butyl)-α- hydroxy-iso- butyramide | 60 60 | 16 16 | — — | 88–90 88–90 | ether/ ether/ chloroform | Colorless |
| D1: Glycolic acid amide | 80– 100 | 4 | $H_2O$ | 115 | ethanol | Beilstein 3,240 |
| D2: N-(2- hydroxy- ethyl)glycolic acid amide | 90– 100 | 16 | — | 72 | methanol | colorless, US Patent 2 347 494 |
| D3: N-(2-hy- droxy-pro- pyl)-glycolic acid amide | 90– 100 | 16 | — | 57 | ethanol | colorless |
| D4: N-(tris- hydroxy- methyl-met- hyl)-glycolic acid amide | 90– 100 | 16 | — | — | — | colorless wax-like |
| D5: N,N-bis- (2-hydroxy- ethyl)- glycolic acid amide | 90– 100 | 16 | — | — | — | Light yel- low resin Belgian Patent 622 170 |
| E1: α,α-bis- hydroxy- methyl-pro- pionic acid amide | 10–20 | 1–2 | methanol | 104–105 | Product washed with chloroform | |
| E2: N-(2-hy- droxyethyl)- α,α-bis-hy- droxymethyl- propionic acid amide | 60 | 24 | — | 1.4732 | — | Light yel- low, vis- cous oil |

The favorable activity of the compounds to be used in accordance with the invention with respect to hygroscopicity and water retention capacity was determined by means of the test methods described below. These methods involve the determination of the equilibrium moisture which is indicative of the water retention capacity, and the determination of the water retention, rehydration and resilience of impregnated pig epidermis.

EXAMPLE 2

(1) Determination of the equilibrium moisture

The substances (approximately 300 to 500 mg) to be tested were moistened with a defined quantity of water and were exposed for 24 hours at 23° C. to various relative atmospheric humidities (1%, 30%, 47%, 65%, 89% and 100% relative humidity). The quantity of water absorbed or desorbed was determined gravimetrically and recorded graphically. The relative humidity at which water is neither given off nor absorbed can be determined from the resultant curves. This value, designated "equilibrium moisture," is a gauge of the capacity of a substance to retain water. The lower the value, the more desirable the substance is from the standpoint of its water retention capacity. Furthermore, the hygroscopicity of the substance can be read from the slope of the curve.

(2) Measurements on pig epidermis (a) Obtaining the pig epidermis

The skin bristles are cut off by means of hair clippers (shearing head of 0.1 mm) immediately after the pigs have been killed. The pigs are soaked for approximately 3 to 5 minutes in water heated to 60° C. The epidermis is subsequently peeled off and stored at −20° C. until it is used.

(b) Determining the water retention and the rehydration of impregnated pig epidermis Punched out pieces of epidermis (1 × 2 cm) were soaked for two hours in a 10% solution of the test substance; excess moisture was removed under standardized conditions by means of a small press; and the pieces were dried for 24 hours, hanging freely between 2 clamps in a 100 ml Erlenmeyer flask at 23° C. and at 30% relative humidity and 50% relative humidity (set by mixtures of sulfuric acid and water). The drying of the impregnated test pieces to X% of the initial weight was compared with the corresponding value of the epidermis which had been soaked only in water (control value). The improvement in the water retention and in the rehydration as compared with the control value is given in Δ% $H_2O$ in the following Table 2. The deviations in each double test amounted to a maximum of ± 2 absolute units. The test was repeated if greater deviations occurred. The rehydration was determined analogously by drying the pig epidermis, which had been impregnated and from which the excess moisture had been removed, for 24 hours at 30% relative humidity, and by subsequent incubation for 24 hours at 90% relative humidity.

(c) Measurement of elasticity of impregnated pig epidermis

Punched-out pieces of epidermis (1 × 6 cm) were soaked for two hours in a 10% aqueous solution of the substance which was to be tested and excess moisture was removed from these pieces under standardized conditions. The test pieces were incubated for 24 hours, hanging freely between 2 clamps at 75% relative humidity and at 90% relative humidity, and were stretched in a Zwick twist-tensile-testing machine (type: 1402) under a load of 0 to 50 pond(p). The expansion in mm, measured in the Hooke range at a load between 5 to 30 pond(p), was used as a gauge for the elasticity.

The measured values obtained in the previously described tests are presented in the following TABLE 2.

TABLE 2

Measurements made on pig epidermis

| Product | Equilibrium moisture (% r.h.) | Water retention in Δ% H$_2$O after drying at | | Rehydration in Δ%H$_2$O absorption at 90% r.h. | mm expansion after loading between 5 and 30 p at | |
|---|---|---|---|---|---|---|
| | | 30% r.h. | 50% r.h. | | 90% r.h. | 75% r.h. |
| Control value | — | 0 | 0 | 0 | 0.3–0.5 | 0 |
| A$_1$ | 74 | 10 | 13 | 31 | 3.2 | 0.9 |
| A$_3$ | 72 | 11 | 17 | 31 | 3.1 | 1.3 |
| A$_4$ | 72 | 11 | 18 | 29 | 4.1 | 1.0 |
| A$_5$ | 72 | 16 | 13 | 23 | 2.8 | 0.7 |
| A$_6$ | 74 | 14 | 17 | 20 | 2.7 | 0.7 |
| A$_7$ | 70 | 10 | 12 | 23 | 3.6 | 1.0 |
| A$_8$ | 69 | 13 | 16 | 24 | 2.0 | 0.5 |
| A$_9$ | 69 | 9 | 15 | 26 | 2.5 | 0.7 |
| B$_1$ | 57 | 9 | 14 | 28 | 3.6 | 1.5 |
| B$_2$ | 58 | 9 | 17 | 28 | 2.8 | 0.7 |
| B$_3$ | 65 | 11 | 12 | 17 | 4.2 | 0.8 |
| B$_4$ | 70 | 8 | 13 | 20 | 4.1 | 1.0 |
| B$_5$ | 65 | 11 | 12 | 22 | 3.8 | 0.7 |
| B$_6$ | 70 | 11 | 12 | 25 | 3.1 | 1.0 |
| B$_7$ | 70 | 10 | 17 | 27 | 3.6 | 0.9 |
| C$_1$ | 70 | 16 | 17 | 26 | 4.5 | 0.5 |
| E$_2$ | 85 | 13 | 14 | 21 | 2.6 | 0.7 |

"—" not measured

In addition to showing the high hygroscopicity of the compounds of the invention, the above Table also shows their considerable water-retention capacity, and thus their eminent suitability for use as agents for keeping the skin moist in preparations for the care, protection and cleansing of the skin.

Some examples of cosmetic preparations containing substances of the invention, as agents for keeping the skin moist, are given below. The quantities of all ingredients are given in parts by weight.

EXAMPLE 3

| Slightly greasy day cream | Parts |
|---|---|
| Fatty acid partial glyceride Cutina MD® Dehydag | 6.0 |
| Stearic acid | 8.0 |
| Mixture of non-ionic emulsifiers Emulgin C 700® Dehydag | 3.0 |
| 2-octyldodecanol | 4.0 |
| Vegetable oil | 3.0 |
| Paraffin oil | 5.0 |
| Triethanolamine | 0.4 |
| 1,2-propylene glycol | 3.0 |
| Product A1 | 6.0 |
| Nipagin M | 0.2 |
| Perfume oil | 1.0 |
| Water | 60.4 |

EXAMPLE 4

| Baby cream | Parts |
|---|---|
| Mixture of higher molecular esters, predominantly mixed esters of pentaerythritol fatty acid ester and citric acid fatty alcohol ester Dehymuls E® Dehydag | 7.0 |
| Decyl oleate | 10.0 |
| Vaseline® | 10.0 |

| Baby cream | Parts |
|---|---|
| Lanolin | 5.0 |
| Boric acid | 0.2 |
| Talc | 12.0 |
| Zinc oxide | 8.0 |
| Nipagin M | 0.2 |
| Product A4 | 8.0 |
| Water | 39.6 |

EXAMPLE 5

| Night cream | Parts |
|---|---|
| Colloidally dispersed mixture of 90 parts of cetyl/stearyl alcohol and 10 parts of sodium lauryl sulfate | 10.0 |
| 2-octyldodecanol | 12.0 |
| Vegetable oil | 7.0 |
| Lanolin | 2.0 |
| Glycerol | 1.0 |
| Product A3 | 10.0 |
| Nipagin M | 0.2 |
| Perfume oil | 1.0 |
| Water | 56.8 |

EXAMPLE 6

| Boro-glycerol cream | Parts |
|---|---|
| Colloidally dispersed mixture of 90 parts of cetyl/stearyl alcohol and 10 parts of sodium lauryl sulfate | 12.0 |
| 2-octyldodecanol | 8.0 |
| Vegetable oil | 5.0 |
| Boric acid | 2.0 |
| Glycerol | 28.0 |
| Nipagin M | 0.2 |
| Product B1 | 6.0 |
| Water | 38.8 |

EXAMPLE 7

| Sun protection cream | Parts |
|---|---|
| Mixture of higher molecular esters with fatty substances Dehymuls K® Dehydag | 30.0 |
| Decyl oleate | 15.0 |
| Light protection agent | 5.0 |
| Nipagin M | 0.2 |

-continued

| Sun protection cream | Parts |
| --- | --- |
| Product B2 | 8.0 |
| Water | 41.8 |

EXAMPLE 8

| Fase Mask | Parts |
| --- | --- |
| Mixture of fatty acid partial glyceride with emulsifiers Cutain LE ® Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product A9 | 10.0 |
| Water | 63.8 |

EXAMPLE 9

| After Shave lotion | Parts |
| --- | --- |
| Oleyl/cetyl alcohol | 1.0 |
| Ethanol 96% | 67.5 |
| Methanol | 0.2 |
| Camphor | 0.2 |
| Peru balsam | 0.1 |
| Perfume | 0.5 |
| Hammamelis extract | 10.0 |
| Boric acid | 0.5 |
| Product A8 | 5.0 |
| Product B6 | 5.0 |
| Water | 10.0 |

EXAMPLE 10

| Face lotion | Parts |
| --- | --- |
| Cucumber juice | 15.0 |
| Citric acid | 0.2 |
| Ethanol 96% | 15.0 |
| Product A8 | 5.0 |
| Product B7 | 5.0 |
| Perfume | 1.0 |
| Water | 58.8 |

EXAMPLE 11

| Foam bath | Parts |
| --- | --- |
| Monoethanolamine lauryl sulfate containing approximately 33% active washing substance | 66.0 |
| Coconut fatty acid diethanolamide | 3.0 |
| Product C1 | 10.0 |
| Perfume oil | 3.0 |
| Water | 18.0 |

EXAMPLE 12

| Cream foam bath | Parts |
| --- | --- |
| Sodium lauryl ether sulfate containing approximately 30% active washing substance | 78.0 |
| Oleic acid diethanolamide | 4.0 |
| Hexyl laurate | 8.0 |
| Product A3 | 5.0 |
| 1,2-propylene glycol | 2.0 |
| Perfume oil | 3.0 |

EXAMPLE 13

Soap containing agents for keeping the skin moist

A mixture of 80% of sodium tallow soap and 20% of sodium coconut soap was used. The soap, in the form of flakes and having a water content of 20%, was mixed with 0.2 parts of 1-hydroxyethane-1,1-diphosphonic acid,
10.0 parts Product A1, and
3.0 parts Perfume oil,
relative to 100 parts by weight of soap, and was deformed in an extrusion press and pressed to form cakes.

EXAMPLE 14

Syndet cake of soap containing agents for keeping the skin moist

The Syndet cake of this example was based on a mixture of olefin sulphonate and sulpho-succinic ester salt. The disodium salt of a sulphosuccinic acid monofatty alcohol ester, produced from the $C_{12}$–$C_{18}$ fraction of a coconut fatty alcohol, was used in preparing the mixture. The olefin sulphonate was derived from a mixture of straight-chain α-olefins having 15 to 18 carbon atoms. This olefin mixture was produced by sulphonation of 1 mole of olefin with approximately 1.2 moles of gaseous sulfur trioxide diluted with an inert gas, hydrolysis of the raw product of sulphonation with the calculated quantity of caustic soda at a temperature of approximately 100° C., and bleaching of the sulphonate by means of hypochlorite. The mixture of the two sulphonates contained approximately 5 percent by weight of neutral salts (sodium sulfate and sodium chloride) relative to the anhydrous sulphonate. The Syndet composition contained the following ingredients:

70 parts by weight of a surfactant mixture of 60 percent by weight of the olefin sulphonate and
40 percent by weight of the disodium salt of the sulphosuccinic acid ester
15 parts by weight of stearic fatty acid (iodine number 2)
2 parts by weight of lanolin
5 parts by weight of water
8 parts by weight of Product A4
2 parts by weight of perfume oil.

The Syndet composition was deformed in an extrusion press and pressed to form cakes.

In place of the compounds used in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A process for maintaining or restoring hygroscopicity in the skin for the care and protection of the skin of warm-blooded animals comprising topically applying to the skin a safe but effective amount as a moisturizer of a cosmetic agent consisting essentially of from 1 to 20 percent by weight, relative to the total agent, of at least one hydroxyalkyl carboxylic acid amide of the formula

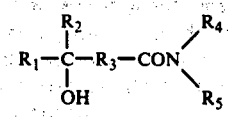

wherein $R_1$ and $R_2$ are independently of each other a member selected from the group consisting of hydrogen and an alkyl radical having 1 to 4 carbon atoms, $R_3$ is a member selected from the group consisting of the direct bond and a straight-chain alkylene radical having 1 to 3 carbon atoms which is optionally substituted by one or more groups selected from the group consisting of alkyl having 1 to 4 carbon atoms and hydroxyalkyl having 1 to 4 carbon atoms, and $R_4$ and $R_5$ independently of one another are a member selected from the group consisting of hydrogen, an alkyl radical having 1 to 4 carbon atoms and an hydroxyalkyl radical having 2 to 6 carbon atoms and 1 to 5 hydroxy groups, and the remainder conventional cosmetic excipients.

2. The process of claim 1 wherein the hydroxyalkyl carboxylic acid amide or mixture of hydroxyalkyl carboxylic acid amides is present in an amount of from 3 to 10% by weight relative to the total agent.

3. The process of claim 1 wherein said conventional cosmetic excipients are selected from the group consisting of emulsifiers, fatty substances, vegetable extracts, preservatives, perfumes, thickeners, solvents, surfactants and mixtures thereof, in the conventional quantities.

4. The process of claim 1 wherein the agent has a slightly acidic pH of about 6.

5. The process of claim 1 wherein the agent is a soap having a weakly alkaline pH.

6. The process of claim 1 wherein $R_1$ and $R_2$ are each hydrogen and $R_3$ is the direct bond.

7. The process of claim 6 wherein the hydroxyalkyl carboxylic acid amide is a member selected from the group consisting of glycolic acid amide, N-(2-hydroxyethyl)-glycolic acid amide, N-(2-hydroxypropyl)-glycolic acid amide, N-(tris-hydroxymethyl-methyl)-glycolic acid amide, and N,N-bis-(2-hydroxyethyl)-glycolic acid amide.

8. The process of claim 6 wherein $R_4$ is hydroxyalkyl and $R_5$ is hydrogen or both $R_4$ and $R_5$ are hydroxyalkyl.

9. The process of claim 1 wherein $R_1$ is methyl, $R_2$ is hydrogen and $R_3$ is the direct bond.

10. The process of claim 9 wherein the hydroxyalkyl carboxylic acid amide is a member selected from the group consisting of lactic acid amide, N-(2-hydroxyethyl)lactic acid amide, N-(2-hydroxypropyl)lactic acid amide, N-(2-hydroxy-isobutyl)lactic acid amide, N-(1,3-di-hydroxy-2-methyl-2-propyl)lactic acid amide, N-(tris-hydroxy-methyl-methyl)lactic acid amide, N,N-bis-(2-hydroxyethyl)lactic acid amide, and N,N-bis-(2-hydroxypropyl)lactic acid amide.

11. The process of claim 9 wherein $R_4$ is hydroxyalkyl and $R_5$ is hydrogen or both $R_4$ and $R_5$ are hydroxyalkyl.

12. The process of claim 1 wherein the hydroxyalkyl carboxylic acid amide is an $\alpha$-, $\beta$-, or $\gamma$- hydroxybutyramide.

13. The process of claim 12 wherein the hydroxyalkyl carboxylic acid amide is an $\gamma$-hydroxybutyramide.

14. The process of claim 13 wherein the $\gamma$-hydroxybutyramide is a member selected from the group consisting of N-(2-hydroxyethyl)-$\gamma$-hydroxybutyramide, N-(2-hydroxypropyl)-$\gamma$-hydroxybutyramide, N-(2-hydroxy-iso-butyl)-$\gamma$-hydroxybutyramide, N-(1,3-dihydroxy-2-methyl-2-propyl)-$\gamma$-hydroxybutyramide, N-(tris-hydroxy-methyl-methyl)-$\gamma$-hydroxybutyramide, N,N-bis-(2-hydroxyethyl)-$\gamma$-hydroxybutyramide, and N,N-bis-(2-hydroxypropyl)-$\gamma$-hydroxy-butyramide.

15. The process of claim 13 wherein $R_4$ is hydroxyalkyl and $R_5$ is hydrogen or both $R_4$ and $R_5$ are hydroxyalkyl.

16. The process of claim 1 wherein the hydroxyalkyl carboxylic acid amide is an $\alpha$- or $\beta$-hydroxyisobutyramide.

17. The process of claim 16 wherein the hydroxyalkyl carboxylic acid amide is an $\alpha$-hydroxyisobutyramide.

18. The process of claim 17 wherein the $\alpha$-hydroxyisobutyramide is a member selected from the group consisting of N-(2-hydroxyethyl)-$\alpha$-hydroxyisobutyramide, N-(2-hydroxypropyl)-$\alpha$-hydroxyisobutyramide and N-(2-hydroxyisobutyl)-$\alpha$-hydroxyisobutyramide.

19. The process of claim 17 wherein $R_4$ is hydroxyalkyl and $R_5$ is hydrogen or both $R_4$ and $R_5$ are hydroxyalkyl.

20. The process of claim 1 wherein the hydroxyalkyl carboxylic acid amide is an hydroxyalkyl propionamide.

21. The process of claim 20 wherein the hydroxyalkyl propionamide is a member selected from the group consisting of $\alpha,\alpha$-bis-hydroxymethyl-propionamide and N-(2-hydroxyethyl)-$\alpha,\alpha$-bis-hydroxymethylpropionamide.

22. The process of claim 20 wherein $R_4$ is hydroxyalkyl and $R_5$ is hydrogen or both $R_4$ and $R_5$ are hydroxyalkyl.

23. A process for maintaining or restoring hygroscopicity in the skin for the care and protection of the skin of warm-blooded animals comprising topically applying to the skin a safe but effective amount as a moisturizer of a cosmetic agent consisting essentially of an emulsion adjusted to a pH between 5 and 7 containing an emulsifier, from 1 to 20 percent by weight, relative to the total agent, of at least one hydroxyalkyl carboxylic acid amide of the formula

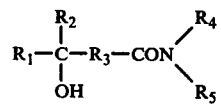

wherein $R_1$ and $R_2$ are independently of each other a member selected from the group consisting of hydrogen and an alkyl radical having 1 to 4 carbon atoms, $R_3$ is a member selected from the group consisting of the direct bond and a straight-chain alkylene radical having 1 to 3 carbon atoms which is optionally substituted by one or more groups selected from the group consisting of alkyl having 1 to 4 carbon atoms and hydroxyalkyl having 1 to 4 carbon atoms, and $R_4$ and $R_5$ independently of one another are a member selected from the group consisting of hydrogen, an alkyl radical having 1 to 4 carbon atoms and an hydroxyalkyl radical having 2 to 6 carbon atoms and 1 to 5 hydroxy groups, and the remainder conventional cosmetic excipients, said emulsion being selected from the group consisting of oil-in-water emulsions and water-in-oil emulsions.

24. A process for maintaining or restoring hygroscopicity in the skin for the care and protection of the skin of warm-blooded animals comprising topically applying to the skin a safe but effective amount as a moisturizer of a cosmetic agent consisting essentially of a water and lower alcohol solution adjusted to a pH between 5 and 7 containing from 1 to 20 percent by weight, relative to the total agent, of at least one hydroxyalkyl carboxylic acid amide of the formula

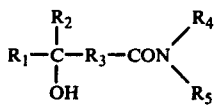

wherein $R_1$ and $R_2$ are independently of each other a member selected from the group consisting of hydrogen and an alkyl radical having 1 to 4 carbon atoms, $R_3$ is a member selected from the group consisting of the direct bond and a straight-chain alkylene radical having 1 to 3 carbon atoms which is optionally substituted by one or more groups selected from the group consisting of alkyl having 1 to 4 carbon atoms and hydroxyalkyl having 1 to 4 carbon atoms, and $R_4$ and $R_5$ independently of one another are a member selected from the group consisting of hydrogen, an alkyl radical having 1 to 4 carbon atoms and an hydroxyalkyl radical having 2 to 6 carbon atoms and 1 to 5 hydroxy groups, and the remainder conventional cosmetic excipients.